(12) United States Patent
Rosenwasser et al.

(10) Patent No.: US 10,869,765 B2
(45) Date of Patent: Dec. 22, 2020

(54) METHODS, INSTRUMENTS AND IMPLANTS FOR SCAPHO-LUNATE RECONSTRUCTION

(71) Applicant: Acumed LLC, Hillsboro, OR (US)

(72) Inventors: Melvin Rosenwasser, Palisades, NY (US); Edward Rosenwasser, Brooklyn, NY (US); Marc von Amsberg, Waxhaw, NC (US); Cate Donaldson, Memphis, TN (US); Matt Schultz, Charles, NC (US)

(73) Assignee: Acumed LLC, Hillsboro, OR (US)

( * ) Notice: Subject to any disclaimer, the term of this patent is extended or adjusted under 35 U.S.C. 154(b) by 248 days.

(21) Appl. No.: 15/759,763

(22) PCT Filed: Sep. 14, 2016

(86) PCT No.: PCT/US2016/051706
§ 371 (c)(1),
(2) Date: Mar. 13, 2018

(87) PCT Pub. No.: WO2017/048826
PCT Pub. Date: Mar. 23, 2017

(65) Prior Publication Data
US 2019/0046328 A1  Feb. 14, 2019

Related U.S. Application Data

(60) Provisional application No. 62/218,387, filed on Sep. 14, 2015.

(51) Int. Cl.
*A61F 2/42* (2006.01)
*A61B 17/72* (2006.01)
(Continued)

(52) U.S. Cl.
CPC ........ *A61F 2/4261* (2013.01); *A61B 17/1782* (2016.11); *A61B 17/7291* (2013.01);
(Continued)

(58) Field of Classification Search
CPC ..... A61B 17/68; A61B 17/8866; A61B 17/86; A61F 2/4261
See application file for complete search history.

(56) References Cited

U.S. PATENT DOCUMENTS

| 5,312,412 A | * | 5/1994 | Whipple | ............ | A61B 17/1782 |
| | | | | | 606/105 |
| 2006/0271054 A1 | | 11/2006 | Sucec et al. | | |

(Continued)

FOREIGN PATENT DOCUMENTS

| CN | 103735306 | 4/2014 |
| CN | 103735306 A | 4/2014 |

(Continued)

OTHER PUBLICATIONS

AU2016322936, "Notice of Acceptance," dated Feb. 12, 2019, 3 pages.

(Continued)

*Primary Examiner* — Jason-Dennis N Stewart
(74) *Attorney, Agent, or Firm* — K&L Gates LLP (57) ABSTRACT

A method for bone reconstruction includes aligning a first hone with a second bone using a plurality of guidewires to correct rotational deformity of the first and second bones. A first module of a targeting apparatus is positioned in proximity to the first bone. A tip of the first module is engaged with the first bone. A second module of the targeting apparatus is positioned in proximity to the second bone. A tip of the second module is engaged with the second bone. Alignment of the first module and the second module is secured. The alignment is verified using a guidewire, the guidewire wire is inserted through a passage extending through the second module. A length between the first bone and the second bone is determined using a depth gauge. An implant is selected based on the determined length for (Continued)

delivery along the passage extending through the second module.

15 Claims, 11 Drawing Sheets

(51) Int. Cl.
  *A61B 17/86* (2006.01)
  *A61B 17/17* (2006.01)
  *A61B 90/00* (2016.01)

(52) U.S. Cl.
  CPC ........ *A61B 17/863* (2013.01); *A61B 17/8685* (2013.01); *A61B 2090/062* (2016.02); *A61F 2002/4289* (2013.01); *A61F 2002/4292* (2013.01)

(56) References Cited

U.S. PATENT DOCUMENTS

| | | | |
|---|---|---|---|
| 2008/0269743 | A1 | 10/2008 | McNamara et al. |
| 2008/0306480 | A1 | 12/2008 | Wilson |
| 2009/0234396 | A1 | 9/2009 | Medoff |
| 2012/0065692 | A1 | 3/2012 | Champagne et al. |
| 2014/0214095 | A1 | 7/2014 | Rosenwasser et al. |
| 2018/0055551 | A1 | 3/2018 | Yalizis |

FOREIGN PATENT DOCUMENTS

| | | | |
|---|---|---|---|
| JP | 2014531936 | A | 12/2014 |
| WO | 2006047541 | A2 | 5/2006 |
| WO | 2015094409 | | 6/2015 |
| WO | 2015094409 | A1 | 6/2015 |
| WO | 2015112124 | A1 | 7/2015 |
| WO | 2017048826 | | 3/2017 |

OTHER PUBLICATIONS

CA2,998,478, "Office Action," dated Feb. 26, 2019, 4 pages.
AU2016322936, "First Examination Report", dated Aug. 13, 2018, 6 pages.
PCT/US2016/051706, "International Search Report and Written Opinion", dated Dec. 7, 2016, 8 pages.
Office Action corresponding to Australian Application No. 2019203570; report dated Sep. 23, 2019; (5 pages).
Office Action corresponding to Brazilian Application No. 1120180050792; report dated Jun. 5, 2020; (5 pages).
Office Action corresponding to Canadian Application No. 2998478, report dated May 29, 2020; (3 pages).
Office Action corresponding to Canadian Application No. 2998478, report dated Nov. 28, 2019; (3 pages).
Office Action corresponding to Chinese Application No. 20160064685.3, report dated May 28, 2019; (25 pages).
Office Action corresponding to Chinese Application No. 20160064685.3, report dated Mar. 3, 2020; (8 pages).
European Search Report corresponding to European Application No. 16847225, report dated Oct. 25, 2019; (10 pages).
Supplementary European Search Report corresponding to European Application No. 1684722.5, report dated Jul. 15, 2019; (12 pages).
Office Action corresponding to Australian Application No. 2019203570; report dated Sep. 17, 2020; (4 pages).
Office Action corresponding to European Application No. 168472215; report dated Jul. 24, 2020; (5 pages).
Office Action corresponding to Japanese Application No. 2018-532543; report dated Aug. 14, 2020; (10 pages).

\* cited by examiner

METHODS, INSTRUMENTS AND IMPLANTS FOR SCAPHO-LUNATE RECONSTRUCTION

CROSS REFERENCE TO RELATED APPLICATIONS

This application is a U.S. 371 of International Application No. PCT/US16/51706, filed Sep. 14, 2016, which application claims the benefit of U.S. Provisional Application No. 62/218,387, filed Sep. 14, 2015, the entire contents of which are hereby incorporated by reference for all purposes in their entirety.

BACKGROUND OF THE INVENTION

Field of the Invention

The subject disclosure relates to methods, surgical instruments and implants for reconstructing the scapho-lunate joint.

Background of the Related Art

Scapho-lunate dissociation is the most common carpal instability. Scapho-lunate dissociation can be characterized by diastases between the scaphoid and lunate bones and rotatory subluxation of the scaphoid. Scapho-lunate dissociation typically causes wrist pain, swelling, clicking, progressive radiocarpal arthritis, and decreased motion and grip strength.

There are currently many surgical treatment options that may be indicated depending on a variety of factors, including healing potential of the ligament, time elapsed since injury, alignment/reducibility of the carpal row and presence/extent of degenerative changes in the wrist. However, all of these treatments have some undesirable results (e.g., loss of range of motion, long periods of immobilization and/or high rates of failure).

One method used to treat scapho-lunate dissociation is dorsal capsulodesis. Dorsal capsulodesis can be performed with or without repair of the scapho-lunate interosseous ligament (SLIL). During either method, a physician temporarily pins Kirschner wires ("K-wires") across the scapho-lunate and scapho-capitate intervals to restore proper carpal alignment during healing. Currently available results indicate that dorsal capsulodesis is associated with long term weakening and provides only limited motion recovery.

Bone-tissue-bone grafts are another treatment option for scapho-lunate dissociation. During the bone-tissue-bone graft procedure, the physician utilizes an autologous bone-tissue-bone graft to replace the scapho-lunate interval. Complications associated with bone-tissue-bone grafts include the problems associated with a second surgical site and selecting a graft that operates similarly to the SLIL being replaced.

As discussed briefly above, prior art methods and medical tools for treating scapho-lunate dissociation have drawbacks. They limit post-operative wrist motion and often prevent subsequent salvage procedures. More recently, the RASL procedure has been found to provide safe and effective treatment for chronic static scapho-lunate dissociation by re-aligning the scaphoid and lunate bones, restoring function, and reducing pain. Currently, surgeons performing the RASL procedure simultaneously use 1.6 millimeter (mm)-thick metal Kirschner wires ("K-wires") to manipulate the bones, a headless cannulated screw to maintain the positioning of the bones post-operatively, and a guide wire to position the screw at the site.

A major difficulty in treating scapho-lunate dissociation using the RASL procedure is that there is very little clearance within the bones for the currently available medical tools used to perform in the procedure (e.g., K-wires, bone clamps, etc), a large number of bones at the site, and a compact area within which to perform the procedure. To wit, there is very little clearance and visibility between the K-wires for the guide wire and the screw, making it difficult and error-prone to properly manipulate the bones using K-wires while leaving enough room for the guide wire and screw to be introduced.

Moreover, the success of the procedure often depends on the surgeon's experience in making educated guesses based on anatomical and biomechanical landmarks and skill in positioning or repositioning the guide wire based on radiographic images. The success is further complicated by the K-wires employed to hold the bones in place getting in the way of the smaller guide wire used to locate the screw, sometimes causing deflection or inhibition.

Still further, identification of the proper position for the guide wire and drilling a pilot hole for the cannulated screw is also difficult and often requires a very skilled surgeon. Ideal placement of the screw is along the axis representing the instantaneous center of motion between the scaphoid and lunate bones in the wrist. Usually, the axis is parallel to the radial inclination and coincident with the mid-waist of the scaphoid and the apex of the lunate. Years of experience are typically required to find the correct axis for the screw.

Therefore, there still remains a need to solve the problems in the art pertaining to the accuracy of implant delivery and implant performance for repair of scapho-lunate tendon injury. More particularly there is a need to solve the challenges associated with bone de-rotation and alignment, and placement of the implant in the bone (trajectory). Further, there is a need to provide an implant that meets most or all of the design requirements of the surgeon, most particularly, one or both of torsional and longitudinal flexibility (bending) of the implant segment between the bones.

SUMMARY

Embodiments herein provide a method for bone reconstruction that includes aligning a first bone with a second bone using a plurality of guidewires to correct rotational deformity of the first and second bones. A first module of a targeting apparatus is positioned in proximity to the first bone. A tip of the first module is engaged with the first bone. A second module of the targeting apparatus is positioned in proximity to the second bone. A tip of the second module is engaged with the second bone. Alignment of the first module and the second module is secured. The alignment is verified using a guidewire, the guidewire wire is inserted through a passage extending through the second module. A length between the first bone and the second bone is determined using a depth gauge. An implant is selected based on the determined length for delivery along the passage extending through the second module.

The method can include inserting a guidewire tube into the passage before insertion of the guidewire. The guidewire and the guidewire tube can be removed from the passage. A path spanning a space between the first and second bone can be formed using a drill inserted through the passage. The implant can be delivered through the path. Securing alignment of the first and second modules can include using one or more knobs. The depth gauge can be a depth gauge on the targeting apparatus.

The implant can include a proximal threaded end and a distal threaded end configured and adapted for insertion into the first and second bones, the proximal threaded end and the distal threaded end can be configured to rotate independently after insertion of the implant into the first and second bones.

The first bone can be a lunate and the second bone can be a scaphoid. The plurality of guidewires can be positioned to rotate the lunate forward and rotate the scaphoid backwards. The plurality of guidewires can be K-wires. The first module can be a lunate engagement module operatively connected to a reduction frame of the targeting guide, the lunate engagement module comprising a lunate pin adapted to grip the lunate. The second module can be a scaphoid engagement module operatively connected to the reduction frame, the scaphoid engagement module having at least a drill tube, an adjustment knob and a fixation seat, the fixation seat can have a set of teeth adapted to grip the scaphoid.

Embodiments herein also provide for a medical apparatus for bone reconstruction including a reduction frame, a first module operatively connected to the reduction frame, the first module comprising a tip for engagement with a first bone, and a second module operatively connected to the reduction frame, the second module comprising a tip or engagement with a second bone and the second module can include a passage extending laterally through for delivery of at least one object.

The second module can include an arm operatively connected to a cannulated fixation seat comprising a set of teeth for engagement with the second bone, the cannulated fixation seat operatively connected to an adjustment knob and a drill tube. The drill tube can be configured to receive one or more additional removable sleeves. The one or more additional sleeves can include a guidewire tube for use in inserting a K-wire through. A drill can be passed through the drill tube to create a path from the first bone to the second bone. A medical implant can be delivered and inserted through the path.

The medical apparatus can also include a frame adjustment knob configured to move the second module towards the second bone for engagement with the second bone. The reduction frame can include a depth gauge for determining a distance spanning the space between the first and second bones. The first module can be a lunate engagement module for engagement with a lunate and the second module is a scaphoid engagement module for engagement with a scaphoid. Each of the lunate engagement module and the scaphoid engagement module can include an arm operatively connected to the reduction frame at one end and connected to the tip at another end.

Still further, embodiments herein provide for an implant assembly including a first threaded end section configured and adapted for insertion into a first bone, a second threaded end section configured and adapted for insertion into a second bone, and an intermediate section operatively connected to the first threaded end section and the second threaded end section. The first threaded end section and the second threaded section are configured to rotate independently after insertion into the first and second bones. The first and second threaded end sections can be configured with different diameters.

These and other features of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those having ordinary skill in the art to which the present disclosure pertains will more readily understand how to employ the devices and methods of the present disclosure, embodiments thereof will be described in detail herein below with reference to the drawings, wherein.

These and other aspects of the subject disclosure will become more readily apparent to those having ordinary skill in the art from the following detailed description of the invention taken in conjunction with the drawings.

DETAILED DESCRIPTION

Disclosed herein are detailed descriptions of specific embodiments of methods, instruments and implant for scapho-lunate reconstruction. It will be understood that the disclosed embodiments are merely examples of the way in which certain aspects of the invention can be implemented and do not represent an exhaustive list of all of the ways the invention may be embodied. Indeed, it will be understood that the systems, devices and methods described herein may be embodied in various and alternative forms. Moreover, the figures are not necessarily to scale and some features may be exaggerated or minimized to show details of particular components.

Well-known components, materials or methods are not necessarily described in great detail in order to avoid obscuring the present disclosure. Any specific structural and functional details disclosed herein are not to be interpreted as limiting, but merely as a basis for the claims and as a representative basis for teaching one skilled in the art to variously employ the invention. Moreover, the devices, instruments and implants are described herein as being used for scapho-lunate reconstruction, but those skilled in the art will appreciate that they can be used in other medical procedures.

Currently, most surgeries involving reconstruction of the scapho-lunate joint are performed free-handed, as there are limited options for tools to properly align the bones and the implant. Embodiments herein provide for a jig assembly/reduction apparatus that is a multi-function tool which allows the surgeon to align and implant a screw properly at the desired depth with the desired trajectory. Furthermore, the jig assembly/reduction apparatus provided herein can measure depth to be used as a guide for other ancillary tools (e.g., drills).

The present disclosure now will be described more fully, but not all embodiments of the disclosure are necessarily shown. In addition, many modifications may be made to adapt a particular situation or material to the teachings of the disclosure without departing from the essential scope thereof.

Figures 4, 5:
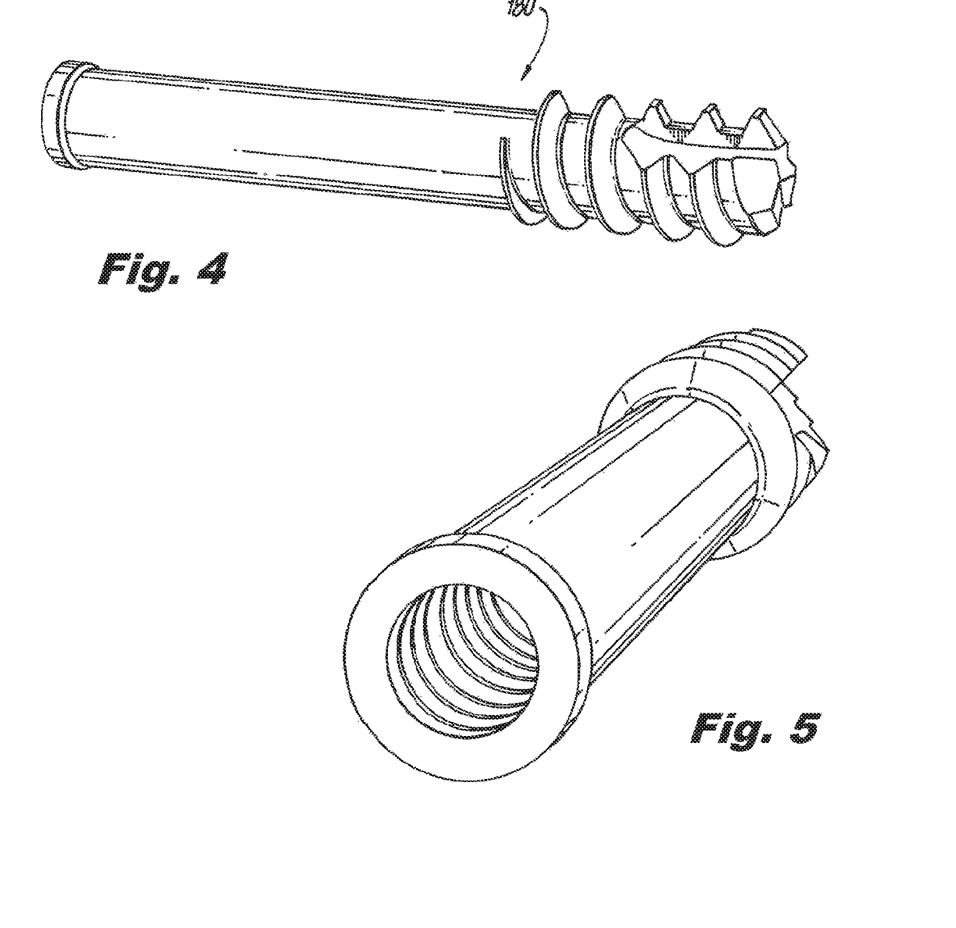
FIG. 4 provides a perspective view taken from an angle of a second tubular threaded end section of the implant assembly of FIG. 1.
FIG. 5 provides a perspective view taken from a different angle of the second tubular threaded end section of the implant assembly of FIG. 1.

Referring to the figures, FIGS. 1-5 show an illustrative implant assembly 150 according to an embodiment herein. The implant assembly 150 includes three main components: a first threaded tubular end section 160, (FIG. 2); a tubular intermediate section 170 (FIG. 3) and a second threaded tubular end section 180 (FIGS. 4 and 5). The first thread tubular section 160 has a series of threads 164 formed on its outer surface and has a drive socket 162 formed at one end and a smooth bore at the other for receiving the tubular intermediate section 170. One end of the tubular intermediate section 170 also includes a drive socket 172 formed at one end and a series of threads 174 formed at the other for engaging with the second threaded tubular section 180. Threads 174 allow the length of the implant assembly to be adjusted and also to allow for some relative rotation and translation between the two ends of the implant assembly 150 once installed.

Figures 1, 2:
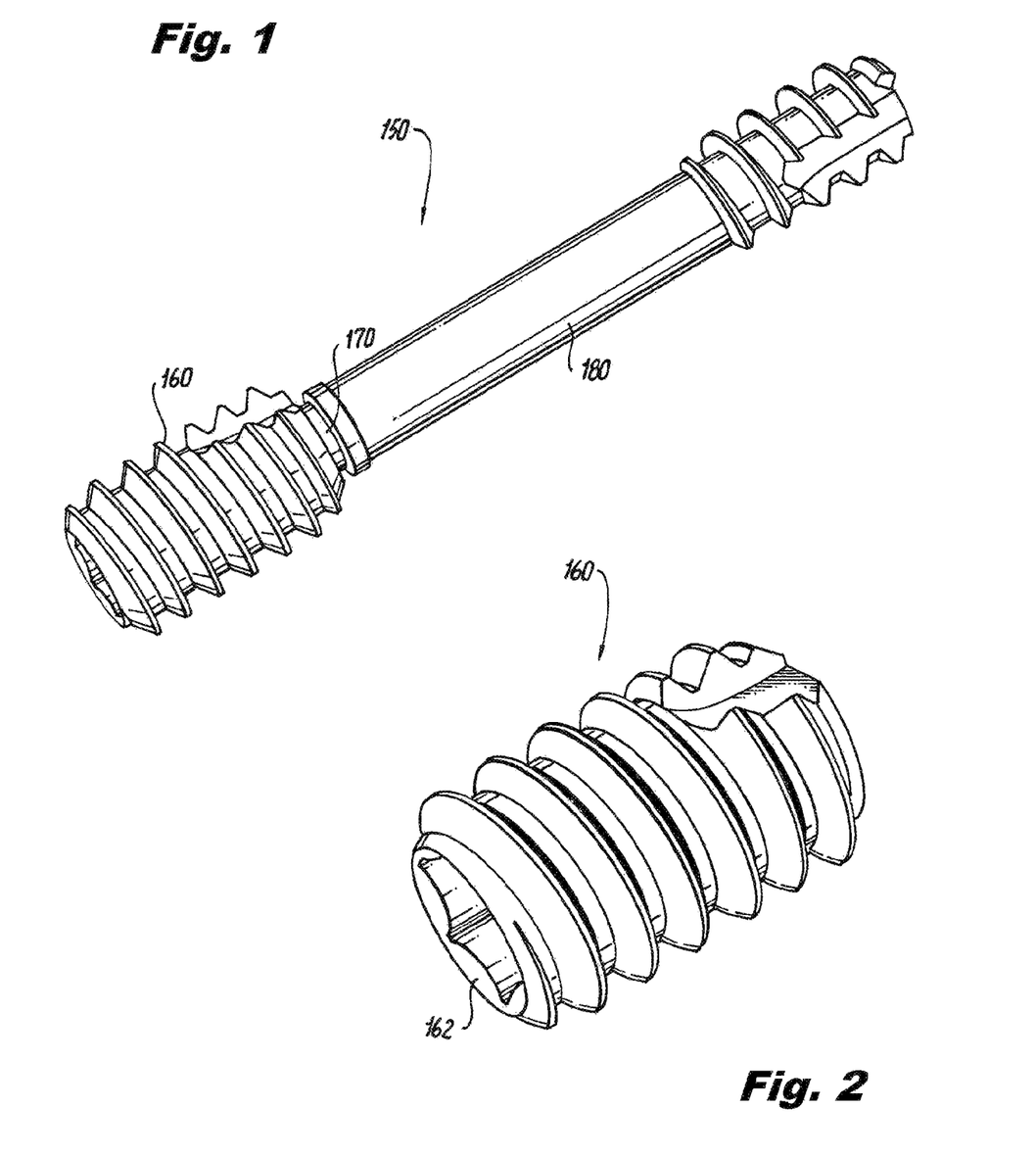
FIG. 1 provides a perspective view of an implant assembly which has been constructed in accordance with an embodiment of the present disclosure.
FIG. 2 provides a perspective view of a first tubular threaded end section for the implant assembly of FIG. 1.
Figure 3:
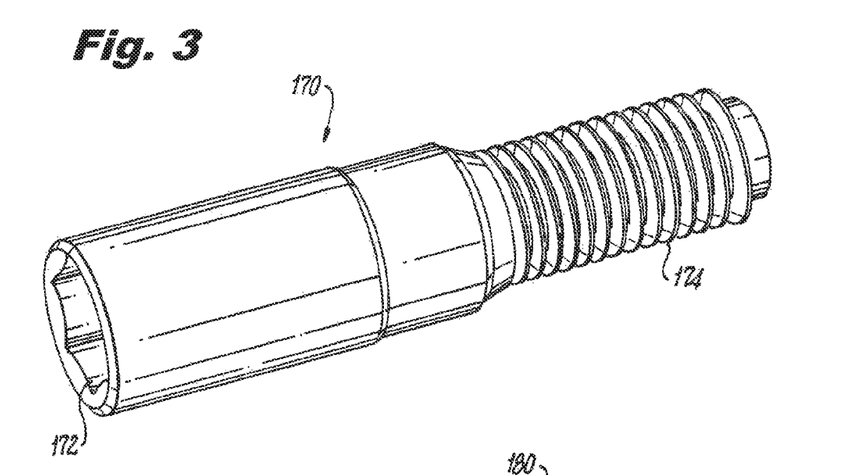
FIG. 3 provides a perspective view of a tubular intermediate section for the implant assembly of FIG. 1.

The first end section 160 of implant assembly 150 can be a proximal threaded end section 160 and the second end section can be a distal threaded section 180, proximal and distal being taken relative to the perspective of a user (e.g., a surgeon). The distal end section 160 is preferably smaller than the proximal end section 160, as the difference in the core diameter and pitch diameter enables the implant assembly 150 to be used as a compression device. When the two threaded ends are of different diameters, after one set of threads crosses the scaphol-unate junction, which is the junction between the scaphoid and lunate bones, it then starts to act as a compressing tool.

Furthermore, implant assembly 150 is designed such that the threaded sections 160 and 180 can rotate freely independent of each other once inserted. The design allows for movement between the two threaded sections 160 and 180 in certain planes (translation), which can be helpful biologically and physiologically in the healing of the ligament being treated.

Figure 16:
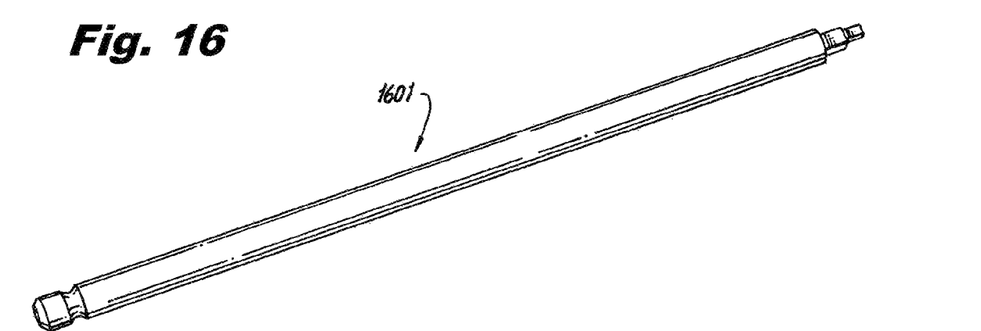
FIG. 16 is a perspective view of a driver bit for use with the implant assembly of FIG. 1.

The implant assembly 150 is a three-piece construction that is welded together during the manufacturing process, the design of the implant assembly 150 allows for a freedom of rotation. Notably, the implant assembly 150 is not a monolithic implant. However, when the implant assembly 150 is inserted using a driver (e.g., driver bit 1601 of FIG. 16), the driver 1601 can drive both thread sections 160 and 180 at the same time. The three-pieces 160, 170 and 180 of the implant assembly 150 are in essence locked together when the implant assembly 150 is inserted (e.g., into the bones). That is, the implant assembly 150 is driven in with a monolithic screw, and once it is in place, the driver is removed and the two thread sections 160 and 180 can rotate in place independently of each other as the joint moves. Optionally, the driver can be used again subsequently to engage either the proximal or distal ends for adjustment or removal of the implant assembly 150.

The implant assembly 150 is designed to be solid (not cannulated, e.g., without a hole in the center), so that it can be smaller and stronger in comparison to traditional bone screws/implant assemblies, and withstand the physiologic forces without breakage. The implant assembly 150 is pre-assembled during manufacture. Once inserted, the two ends of the implant assembly 150 can rotate freely from each other. The implant assembly 150 can be available in various sizes and/or lengths to accommodate differences in size of the spanned scaphoid and lunate.

Referring now to FIGS. 6-13, which illustrate a targeting guide 100 which has been constructed in accordance with an embodiment of the present disclosure. As will be described below, targeting guide 100 can be used in a RASL procedure.

Figure 6:
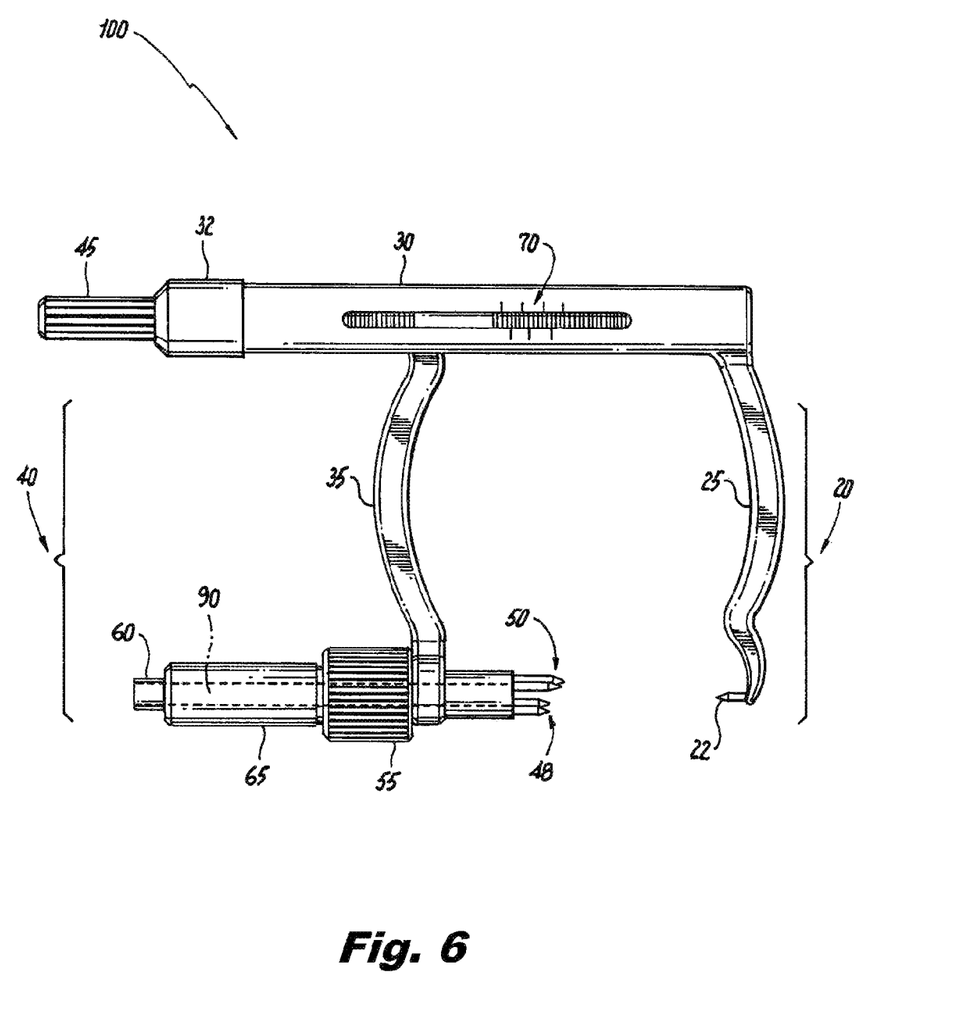
FIG. 6 provides a side elevation of a targeting guide assembly which has been constructed in accordance with an embodiment of the present disclosure.
Figures 7, 8, 9:
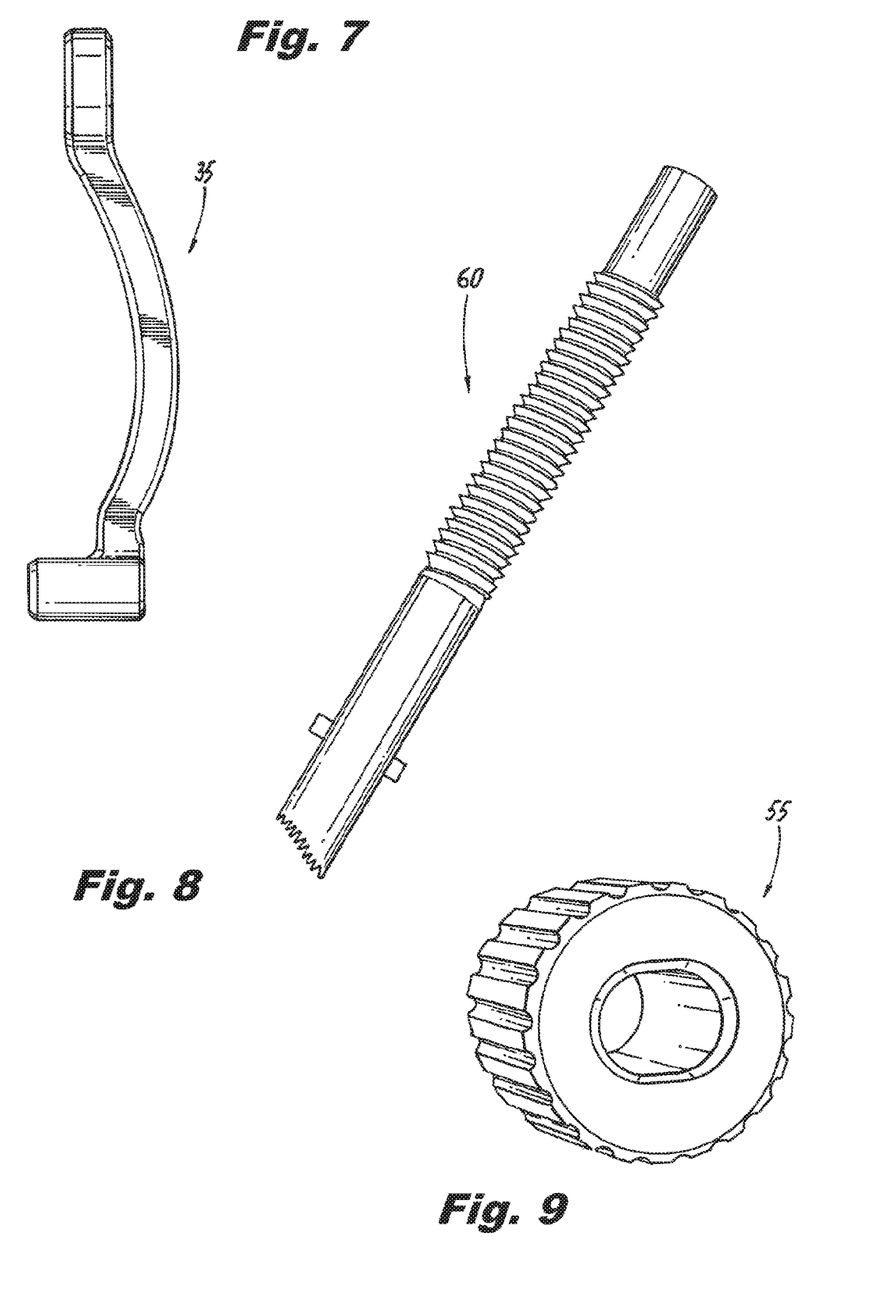
FIG. 7 provides a perspective view of an arm associated with a scaphoid engagement module used in the targeting guide assembly of the FIG. 6.
FIG. 8 provides a perspective view of a drill tube associated with a scaphoid engagement module used in the targeting guide assembly of the FIG. 6.
FIG. 9 provides a perspective view of a knob associated with a scaphoid engagement module used in the targeting guide assembly of the FIG. 6.
Figure 13:
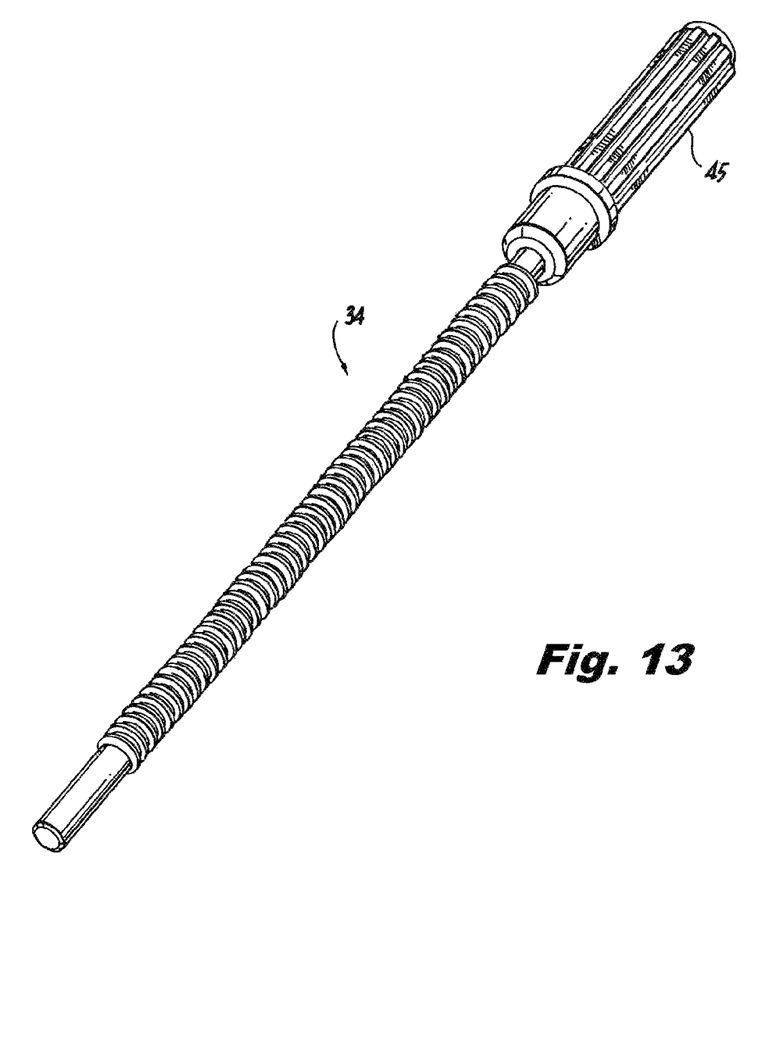
FIG. 13 provides a perspective view of threaded adjustment rod used with the reduction frame of targeting guide assembly of the FIG. 6.

Targeting guide 100 is a multi-function tool for scaphoid and lunate bone engagement and manipulation, and implant guidance. Targeting guide 100 includes a reduction frame 30 (FIG. 11) operatively connected to a cap 32 (FIG. 12) and an adjustment portion having a frame adjustment knob 45 operatively connected to a threaded drive rod 34 (FIG. 13). The reduction frame 30 includes an implant depth gauge 70 (FIG. 6). The reduction frame 30 includes a lunate engagement module 20 at an end opposite from the frame adjustment knob 45. The lunate engagement module 20 includes a lunate jig 25 operatively connected to a lunate engagement pin 22 at one end.

Figure 10:
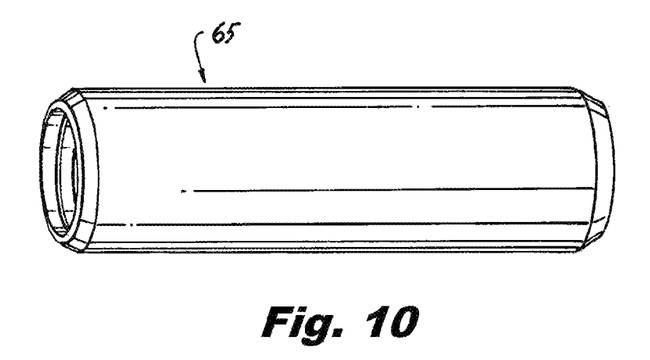
FIG. 10 provides a perspective view of a lock nut associated with a scaphoid engagement module used in the targeting guide assembly of the FIG. 6.
Figures 11, 12:
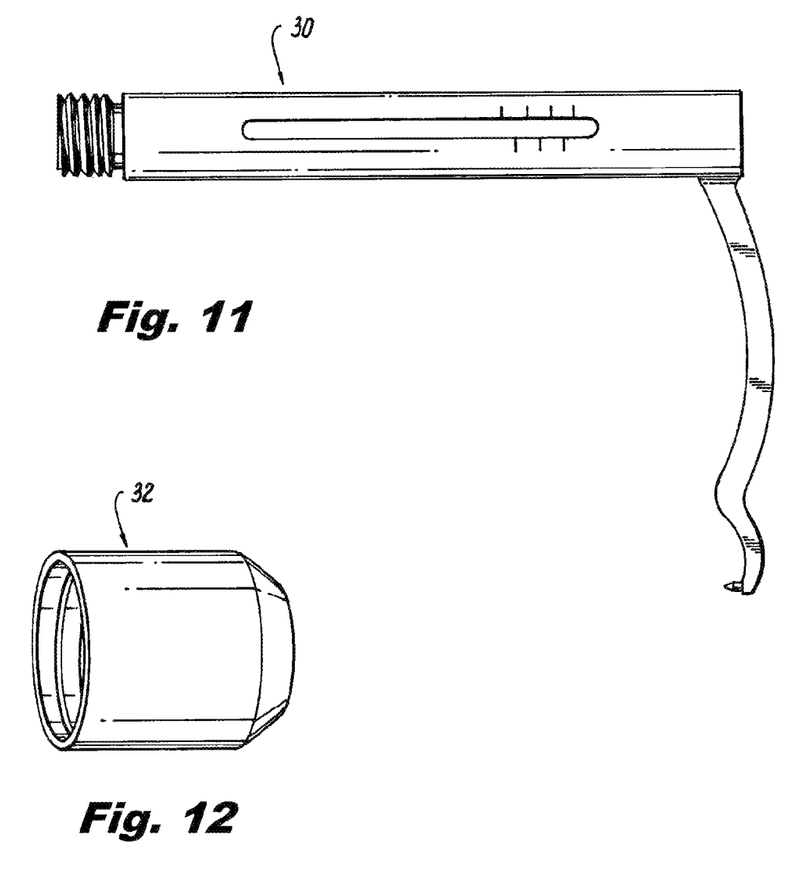
FIG. 11 provides a perspective view of a reduction frame and a lunate engagement module used in the targeting guide assembly of the FIG. 6.
FIG. 12 provides a perspective view of a cap associated with the reduction frame used in the targeting guide assembly of the FIG. 6.

The targeting guide 100 also includes a scaphoid engagement module 40 in operative engagement with the reduction frame 30. The scaphoid engagement module 40 includes an arm 35 (FIG. 7), a threaded drill tube 60 that includes a fixation seat 48 and teeth 50 (FIG. 8), a knob 55 (FIG. 9), a lock nut 65 (FIG. 10). Threaded drill tube 60 is configured to receive drill guide tubes 1801 and 1901 shown in FIGS. 18 and 19. Notably, components 60, 55 and 48 are each hollow, thereby forming a continuous path 90 (represented by dotted lines in FIG. 6) through which tools (e.g., guide wire, drill) and implants may pass through.

In embodiments herein, the targeting guide 100 aids in alignment of the bones, while the guidewire acts as an initial targeting guide before making the commitment to drill a hole. In many existing systems, a guide wire (e.g., K-wire) is placed, a hole is drilled and a screw (e.g., implant assembly 150) is then placed over it, which means the screw has to be cannulated with a hole in the middle to accommodate the guide wire. Advantageously, in embodiments herein, the guidewire is only used as a last check prior to embarking on commitment to a screw path. The entire targeting guide 100 is used to realign the bones, and then a guide wire is placed and assessed on X-ray to see if the guidewire is headed where the screw is intended to go ultimately. The guide wire is subsequently removed and the screw path 90 is generated by a drill, the screw is then inserted through the screw path 90. Notably, the guidewire is no longer present in the screw path 90 at the end of the operation, as it is in various existing methods.

Figure 20:
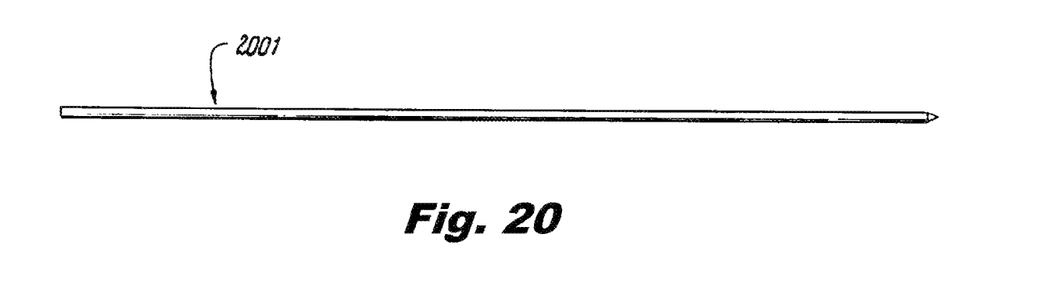
FIG. 20 is a perspective view of a 1.5 mm K-wire for use with the targeting guide assembly of the FIG. 6.
Figure 21:
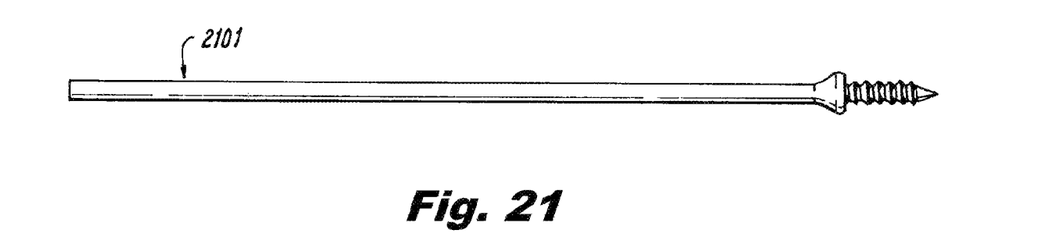
FIG. 21 is a perspective view of an alternate wire (olive) for use with the reduction of bones, e.g., the scaphoid and lunate bones.

In certain instances, the alignment can be manipulated (reduced) from a displaced posture by using additional wires (e.g., wires: 2001, and 2101 of FIGS. 20 and. 21) which are outside the plane of where the screw is heading. The additional wires can be used as "joysticks." similar to manipulation tools to manipulate the bones into position. The targeting guide 100 can then be applied to the reduced alignment of the two bones and the device 100 holds them in that position by a squeezing/trapping mechanism. At this point the "joysticks" are no longer necessary and can be removed once the jig apparatus is in place.

Figure 17:
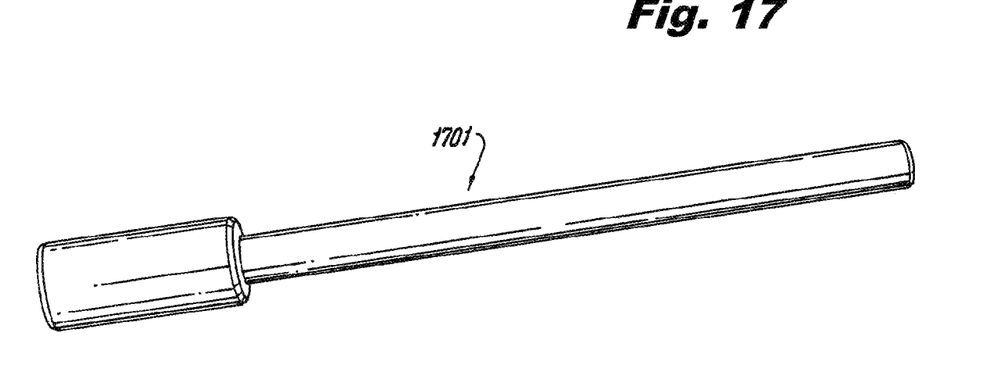
FIG. 17 is a perspective view of a K-wire guide tube for use with the targeting guide assembly of the FIG. 6.
Figure 22:
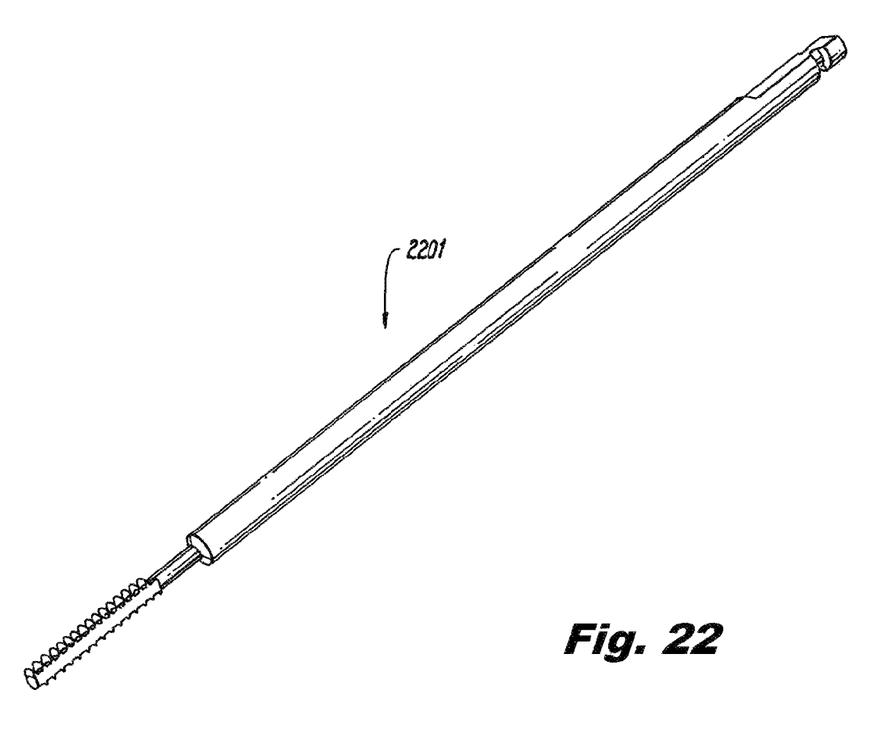
FIG. 22 is a perspective view of a 3.5 mm tap for use with the targeting guide assembly of the FIG. 6.

Once the scaphoid and lunate bones are reduced/aligned, the targeting guide 100 can be applied to a specific geographic location of each of the two bones independently. The targeting guide 100 is designed with specific capturing points which are positioned at the lunate and scaphoid at specific locations, these point are visually documented and also checked by X-ray. The capturing points are shown as teeth 50 on fixation seat 48 on the scaphoid lunate engagement module 40 and as lunate engagement pin 22 on the lunate engagement module 20. The capturing points are applied in specific positions anatomically according to visual and x-ray cues and landmarked, then these points are assessed by x-ray in two planes. At this point, the targeting guide 100 is tightened and secured using knob 55, the bones are held in place to allow a surgeon to see the intended path of the screw. A K-wire 2001 is placed inside the targeting guide 100 through a sleeve (e.g., K-wire guide tube 1701 shown in FIG. 17), and then check by X-ray. The K-wire 2001 and the K-wire guide tube 1701 are removed, the implant assembly 150 is positioned first with a drill 1601 and then a tap (e.g., tap 2201 shown in FIG. 22) or no-tap based on bone quality and the implant assemble 150 is inserted.

Figure 14:
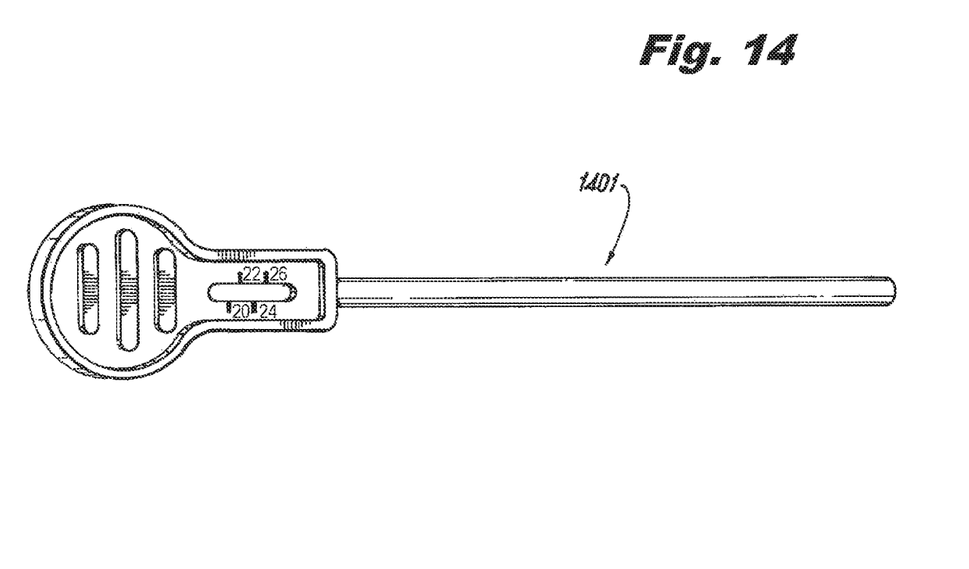
FIG. 14 provides a perspective view of a K-wire depth gauge for use with the targeting guide assembly of the FIG. 6.
Figure 15:
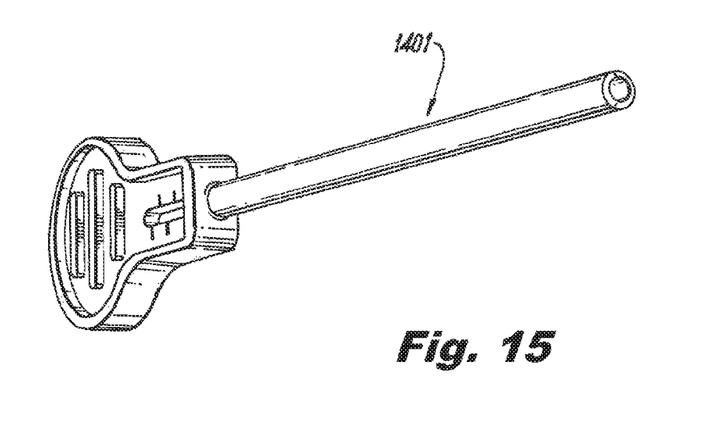
FIG. 15 provides another perspective view of the K-wire depth gauge of FIG. 14.
Figure 18:
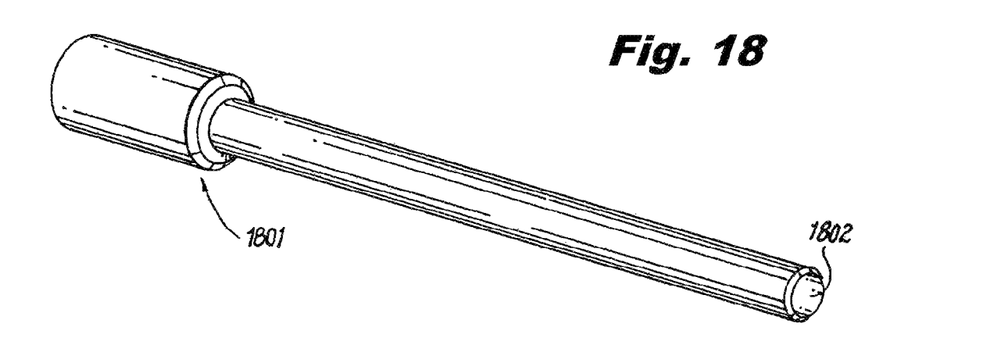
FIG. 18 is a perspective view of a 3.7 mm drill guide tube for use with the targeting guide assembly of the FIG. 6.
Figure 19:
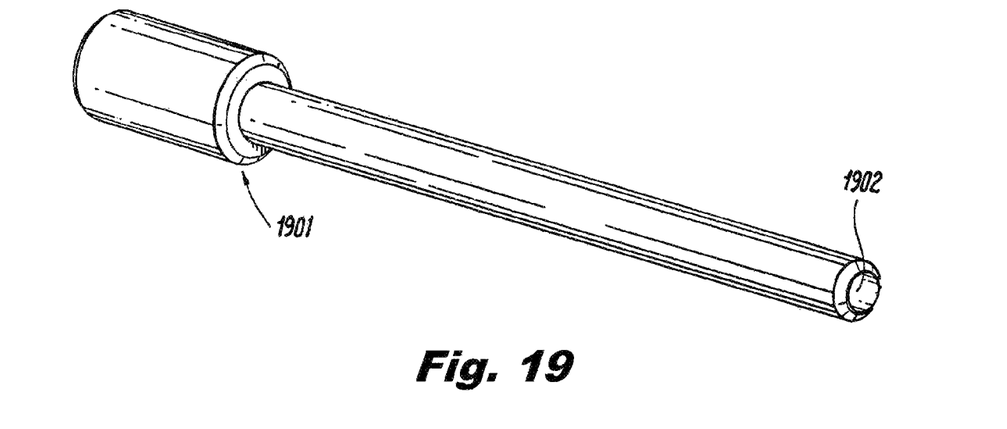
FIG. 19 is a perspective view of a 2.7 mm drill guide tube for use with the targeting guide assembly of the FIG. 6.
Figure 23:
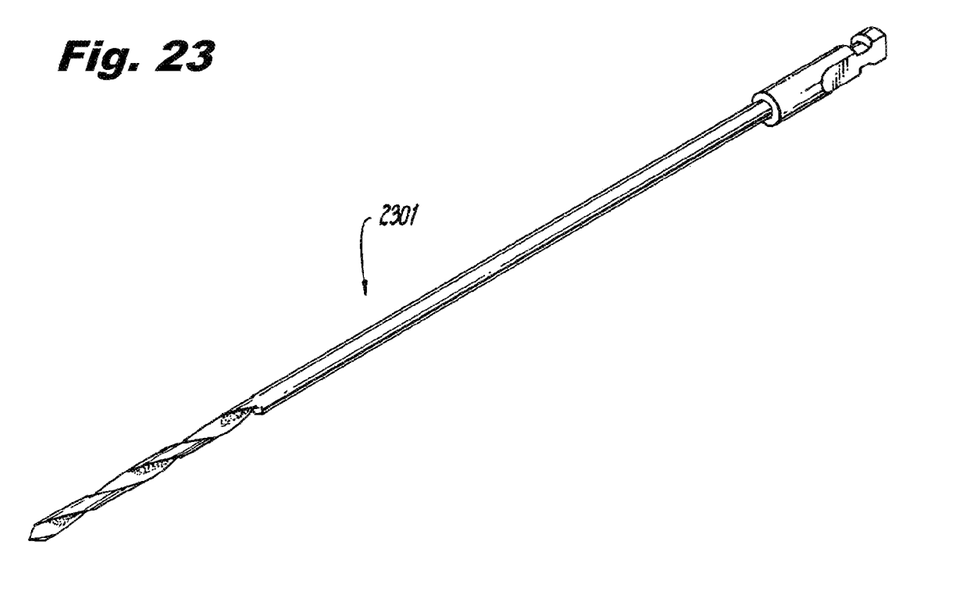
FIG. 23 is a perspective view of a 2.5 mm drill for use with the targeting guide assembly of the FIG. 6.
Figure 24:
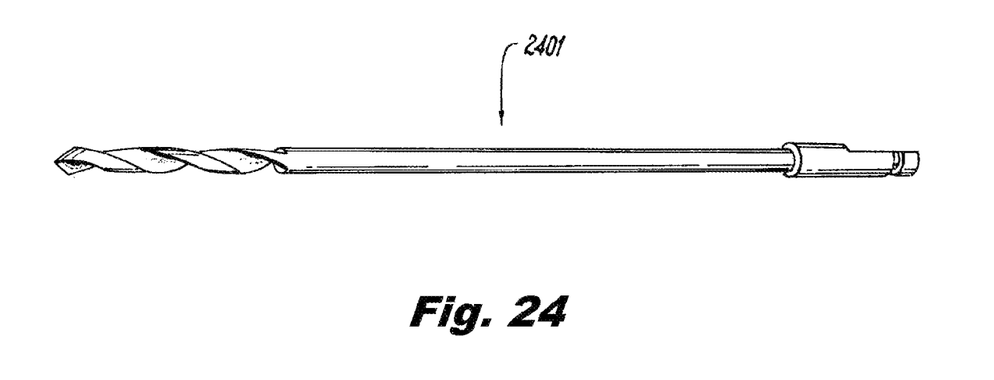
FIG. 24 is a perspective view of a 3.5 mm drill for use with the targeting guide assembly of the FIG. 6.

Targeting guide 100 includes a path 90 for the tools to pass through. FIGS. 18 and 19 show drill guide tubes 1801 and 1901, which can be a 3.7 mm or 2.7 mm drill guide tube, respectively. The drill guide tubes shown in FIGS. 18 and 19 can be used for two different drills. The drill guide tube 1801 or drill guide tube 1901 can be inserted into drill tube 60, each of drill guide tube 1801 and drill guide tube 1901 can include a receptacle 1802 and receptacle 1902, respectively, through which a drill (e.g., a 2.5 mm drill 2301 as shown in FIG. 23 or a 3.5 mm drill 2401 shown in FIG. 24) can fit through. A removable sleeve can be fitted into the receptacle 1802 or 1902, which is smaller and can be used for the guidewire (e.g., K-wire 2001). The K-wire dimensions are much smaller than the drill so the K-wire guide tube (e.g., K-wire guide 1701 tube of FIG. 17) is provided as a smaller insert that can be removed when the K-wire is removed. The drill itself can then go through the drill tube 60 and drill guide tube 1801 or 1901 (depending on the size of the drill), thereby forming the path 90 for delivery of the implant assembly 150 through the path 90. The teeth 50 at the end of fixation seat 48 grips the bone so as to prevent the device from sliding and rotating, corresponding point 22 on the lunate side also grips the lunate, thereby gripping the two bones together. The rotating knob 55 aids in locking the targeting guide and bones together, and the distance between the scaphoid and lunate bones are determined using the scale of implant depth gauge 70 on the reduction frame 30 and/or a depth gauge 1401 as shown in FIGS. 14 and 15.

As described above, the sleeves/inserts are of different diameters to accommodate for the different diameter tools being used, i.e., a tube-within-a-tube configuration. The aperture at the end is pointed at the target where the implant assembly should ultimately be placed.

Advantageously, once the bones are reduced or aligned, the targeting guide 100 can hold them in place and everything being done after this point is done with the proper orientation of the two bones, thus avoiding rotational deformity of the bones. As such, the targeting guide 100 is critical not only to have a path for the tools and implants to pass through, but also for the final alignment placement of the implant.

A representative, method for operation of the targeting guide 100 is as follows:

1. Dissect on the dorsal surface of the hand to expose the scaphoid and lunate bones;

2. Drive guidewires (e.g., K-wires of FIG. 20 and/or wire 2101 of FIG. 21) into both the scaphoid and lunate bones. Then manipulate the K-wires to align the scaphoid and lunate bones. The K-wires are placed in such a way that the scaphoid can be rotated backwards and the lunate forward to correct for any rotational deformity caused by the carpal instability;

3. Position the lunate engagement module 20 with the arm of the lunate jig 25 in proximity to the medial aspect of the lunate. Align the tip of the lunate engagement pin 22 with the apex of the lunate (central position) and insert the pin into the lunate;

4. With the reduction frame 30 fully extended, position the scaphoid engagement module 40 in proximity to the lateral aspect of the scaphoid and advance toward the scaphoid by rotating the frame adjustment knob 45 until the teeth 50 of cannulated conformal fixation seat 48 teeth rest on, but do not penetrate the lateral aspect of the scaphoid;

5. Articulate knob 55 to rotate the angulated face of fixation seat 48. It has been found that adjusting the position of the angulated face of fixation seat 48 to better mate with the scaphoid curvature improves the reduction procedure. The angled surface mimics the scaphoid curvature and stabilizes the engagement of the fixation seat 48 to the bone;

6. Initiate the reduction process by further rotation of adjustment knob 45 to advance the conformal fixation seat 48 to engage the teeth 50 into the scaphoid to gain purchase into the bone;

7. Once the proper position of the fixation seat 48 has been established, adjust lock nut 65 so as to prevent further rotation of the seat 48. Securing the lock nut also locks the alignment of the assembly in relation to the hand (e.g., the targeting guide 100 is laid against the patients forearm or hand) and out of the surgical field and x ray beam when utilized;

8. With the bones fully reduced and locked into place, read the implant depth gauge 70 provided on the frame 30 to determine the distance between the lateral surface of the scaphoid and the medial surface of the lunate;

9. A K-wire guide tube 1701 may be inserted into the drill tube if needed. Place the K-wire 2001 into the K-wire guide tube 1701 and check the alignment of the instrument. Then, slide the depth gauge 1401 over the K-wire 2001 to check the screw length. Then remove the depth gauge 1401. K-wire guide tube and K-wire, and sequentially tap then drill the hole for the implant path 90. FIGS. 18-24 illustrate drill guide tubes, taps and drills that can be used for this procedure and inserted into the central bore formed in the drill tube 60:

10. Select an implant length for use based on the reading from the implant depth gauge to determine the corresponding implant length and then the surgeon would subtract a length (e.g., 2 mm) to allow for the screw to be slightly recessed within the bone;

11. Load the implant assembly 150 shown in FIGS. 1-5 onto the driver (FIG. 16) and engage both drive sockets 162 and 172;

12. Use the implant guide in engagement with the drill guide to guide and deliver and install the implant assembly 150 along the path 90 through the scaphoid module.

It is believed that the present disclosure includes many other embodiments that may not be herein described in detail, but would nonetheless be appreciated by those skilled in the art from the disclosures made. Accordingly, this disclosure should not be read as being limited only to the foregoing examples or only to the designated embodiments.

What is claimed is:

1. A method for bone reconstruction to correct a rotational deformity and enhance anatomical joint stability, comprising:
    driving a first guidewire into a first bone;
    driving a second guidewire into a second bone; wherein the first bone is adjacent to the second bone, the bones forming an anatomical joint;
    aligning the first bone with the second bone using the respective guidewires to correct the rotational deformity and enhance stability of the first and second bones;
    positioning a first module of a targeting guide in proximity to the first bone;
    engaging a tip of the first module with the first bone;
    positioning a second module of the targeting apparatus in proximity to the second bone;
    engaging a tip of the second module with the second bone;
    securing alignment of the first module and the second module;
    verifying alignment using a third guidewire, wherein the third guidewire wire is inserted through a passage extending through the second module without being inserted into the first or second bone;
    determining a length between the first bone and the second bone using a depth gauge; and
    selecting an implant based on the determined length for delivery along the passage extending through the second module.

2. The method of claim 1, further comprising inserting a guidewire tube into the passage before insertion of the third guidewire.

3. The method of claim 2, further comprising removing the third guidewire and the guidewire tube from the passage.

4. The method of claim 3, further comprising delivering the implant through the path.

5. The method of claim 1, wherein the implant is a three-piece modular implant comprising:
    a proximal threaded end;
    a distal threaded end; and
    an intermediate section operatively connected between the proximal threaded end and the distal threaded end; wherein the proximal threaded end and the distal threaded end are configured and adapted for insertion into the first and second bones, the proximal threaded end and the distal threaded end configured to rotate independently after insertion of the implant into the first and second bones.

6. The method of claim 1, wherein the first bone is a lunate bone and the second hone is a scaphoid bone.

7. The method of claim 6, wherein correcting rotational deformity of the first and second bones include reducing the lunate and scaphoid bones, respectively.

8. The method of claim 6, wherein the first module is a lunate engagement module operatively connected to a reduction frame of the targeting guide, the lunate engagement module comprising a lunate pin adapted to grip the lunate bone.

9. The method of claim of claim 8, wherein the second module is a scaphoid engagement module operatively connected to the reduction frame, the scaphoid engagement module comprising a drill tube, an adjustment knob and a fixation seat, the fixation seat including a set of teeth adapted to grip the scaphoid bone.

10. The method of claim 1, further comprising:
    removing the third guidewire from the passage; and
    forming a path between the first and second bone using a drill inserted through the passage subsequent to removing the third guidewire from the passage.

11. A medical apparatus for bone reconstruction, comprising:
    a reduction frame;
    a first module operatively connected to the reduction frame, the first module comprising a first tip configured to engage a first bone; and
    a second module operatively connected to the reduction frame, the second module comprising a second tip configured to engage a second bone and a passage extending laterally therethrough for delivery of at least one object, wherein the passage is parallel to the reduction frame.

12. The medical apparatus of claim 11, wherein the second module comprises an arm operatively connected to a cannulated fixation seat comprising a set of teeth for engagement with the second bone, the cannulated fixation seat operatively connected to an adjustment knob and a drill tube.

13. The medical apparatus of claim 12, further comprising a frame adjustment knob configured to move the second module towards the second bone for engagement with the second bone.

14. The medical apparatus of claim 11, wherein the reduction frame comprises a depth gauge for determining a distance between the first and second bones.

15. The medical apparatus of claim 11, wherein the first tip or the second tip is adjustable.

* * * * *